United States Patent [19]
Ichikawa et al.

[11] 3,983,159
[45] Sept. 28, 1976

[54] PROCESS FOR PRODUCING BIPHENYLPOLYCARBOXYLIC ACID ESTER

[75] Inventors: Yataro Ichikawa, Iwakuni, Japan; Teizo Yamaji, Potsdam, N.Y.

[73] Assignee: Teijin Limited, Osaka, Japan

[22] Filed: Aug. 16, 1974

[21] Appl. No.: 498,182

Related U.S. Application Data

[62] Division of Ser. No. 56,966, July 21, 1970, Pat. No. 3,857,874.

[52] U.S. Cl. .......................... 260/473 R; 260/475 R
[51] Int. Cl.$^2$ ......................................... C07C 67/00
[58] Field of Search ..................... 260/473 R, 475 R

[56] References Cited
UNITED STATES PATENTS

| | | | |
|---|---|---|---|
| 3,145,237 | 8/1964 | Van Helden et al. | 260/475 R |
| 3,303,020 | 1/1967 | Clement et al. | 260/597 B |
| 3,401,207 | 9/1968 | Selwitz | 260/670 |
| 3,428,700 | 2/1969 | Cyba | 260/670 |
| 3,539,622 | 11/1970 | Heck | 260/475 R |
| 3,636,168 | 1/1972 | Josephson | 260/670 |
| 3,857,874 | 12/1974 | Ichikawa et al. | 260/475 |

OTHER PUBLICATIONS

Moiseev et al., Daklady Akademii Nawk SSSR, vol. 130, (1960) pp. 820–823 (Trans).
Hartley, Chem. Rev., 67, 799, 824 (1969).
Ichikawa et al., Nippon Kayaku Zasshi, 90(2), (1969) pp. 212–218.
Van Helden et al., Rec. Trav. Chim., 84, (1965) p. 1263.
Davidson et al., J. Chem. Soc., Sect. A, (1968) p. 1324.
Davidson et al., J. Chem. Soc., Sect. A, (1968) p. 1331.
Davidson et al., Chem. & Ind., (1967) p. 1361.
Ichikawa et al., Chem. Abst., 70:96310v, (1969).

*Primary Examiner*—Lorraine A. Weinberger
*Assistant Examiner*—Michael Shippen
*Attorney, Agent, or Firm*—Sherman & Shalloway

[57] ABSTRACT

The oxidative coupling of benzenecarboxylic acid esters to form the corresponding biphenylpolycarboxylic acid esters, comprising contacting a benzenecarboxylic acid ester having at least one hydrogen atom bonded to the nuclear carbon atom of the benzene ring, such as methyl benzeate, with molecular oxygen in a liquid phase using a catalyst comprising at least one compound selected from organic carboxylates of palladium, such as palladium acetate and β-dikete complexes of palladium, such as acetylacetone-palladium complex. Use of at least one zirconium compound, such as zirconium oxystearate in conjunction with the catalyst gives rise to an increased catalytic activity.

8 Claims, No Drawings

PROCESS FOR PRODUCING BIPHENYLPOLYCARBOXYLIC ACID ESTER

This is a division of application Ser. No. 56,966, filed July 21, 1970, now U.S. Pat. No. 3,857,874.

This invention relates to a process for producing biphenylpolycarboxylic acid esters by contacting benzene-carboxylic acid esters containing at least one hydrogen atom bonded to the nuclear carbon atom with molecular oxygen, thereby affecting oxidative dimerization.

The method of producing biphenylpolycarboxylic acid esters by oxidative coupling of benzene carboxylic acid esters is interesting both scientifically and technologically.

It has heretofore been known to prepare biphenyl compounds by dimerizing aromatic compounds such as benzene, toluene, or methyl benzoate in the presence of palladium chloride and an acid binder such as sodium acetate. The use of palladium chloride and an acid binder such as an alkali salt, however, poses a serious problem of corrosion of equipment by palladium chloride.

In the prior art process described above, the palladium compound acts mainly as a reactant of stoichiometrical amount, and the palladium compound which has participated in the coupling reaction is reduced to a low valency state. Thus, it does not have a high valency effective for the coupling in the reaction system, and cannot act catalytically.

Accordingly, a primary object of the present invention is to provide a process for producing biphenylpolycarboxylic acid esters by oxidative coupling of benzenecarboxylic acid esters using molecular oxygen in the presence of a palladium compound catalyst exclusive of palladium chloride which poses a problem of corrosion.

According to the present invention, biphenylpolycarboxylic acid esters can be catalytically produced by contacting a benzenecarboxylic acid ester having at least one hydrogen atom bonded to the nuclear carbon atom with molecular oxygen in a liquid phase in the presence of a catalyst selected from the group consisting of (a) organic carboxylates of palladium and (b) β-diketo complexes of palladium.

The benzenecarboxylic acid esters used as the starting materials in the process of the invention may be any benzenecarboxylic acid esters which have at least one hydrogen atom attached to the nuclear carbon atom of the benzene ring. The preferred examples are benzene-mono- or -di-carboxylic acid esters, and the benzenemonocarboxylic acid esters give especially good results. These benzene-mono- or -di-carboxylic acid esters may contain at least one substituent inert to the reaction of the present invention, such as alkyl, alkoxy, or halogen.

The benzenecarboxylic acid esters which are used as the starting materials with especially good results are expressed by the following formula

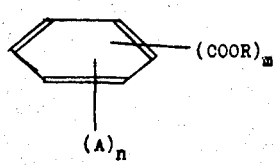

wherein R's may be the same or different and represent an alkyl group having 1–4 carbon atoms, $m$ is an integer of 1 or 2, A's may be the same or different and represent an alkyl group having 1–4 carbon atoms, an alkoxy group having 1–4 carbon atoms, or a halogen atom, $n$ is an integer of 0 to 3, the sum of $m$ and $n$ does not exceed 4, and when $n$ is 0, $(A)_n$ represents a hydrogen atom.

Examples of the starting materials of the present invention which are especially readily available and can be oxidatively coupled with good results by the process of the invention include, for instance, benzoates such as methyl benzoate, ethyl benzoate, propyl benzoate and butyl benzoate, toluylates such as methyl o-toluylate, ethyl o-toluylate, propyl o-toluylate, butyl o-toluylate, methyl m-toluylate, propyl m-toluylate, butyl m-toluylate, methyl p-toluylate, ethyl p-toluylate, propyl p-toluylate, and butyl p-toluylate, methyl dimethylbenzoate, methyl trimethylbenzoate, methyl monochlorobenzoate, methyl monomethoxybenzoate, methyl dimethoxybenzoate, dimethyl phthalate, and dimethyl isophthalate.

The reaction by the process of the invention of oxidatively coupling the aforementioned starting materials is performed in a liquid phase either in the presence or absence of solvent. When the reaction is carried out in the absence of a solvent, the reaction system is maintained liquid by the starting materials, and when it is carried out using a solvent, an organic liquid medium which is stable under the reaction conditions and inert to the reaction of the present invention is employed.

In the present invention, the oxidative coupling of the starting materials described above is carried out in the presence of a catalyst comprising at least one compound selected from the group consisting of (a) organic carboxylates of palladium and (b) β-diketo complexes of palladium. The organic carboxylates of palladium may be any of those which are at least partially soluble in the reaction system of the invention. Organic carboxylic acids which provide acid residues of such organic carboxylates may include aliphatic carboxylic acids, alicyclic carboxylic acids and aromatic carboxylic acids; they may not only be monocarboxylic acids, but also dibasic or polybasic carboxylic acids. Examples of the organic carboxylates of palladium which are conveniently used in the process of the invention are:

i. Aliphatic monocarboxylates having 1–20 carbon atoms such as formate, acetate, trifluoroacetate, monochloroacetate, propionate, n- or iso-butyrate, laurate, palmitate, and stearate;

ii. Aliphatic carboxylates such as naphthenate, cyclohexanemonocarboxylate, and methyl cyclohexanemonocarboxylate; and iii. Benzenecarboxylates or naphthalenecarboxylates such as benzoate, o-, m-, or p-toluylate, phthalate, p-tertiary butylbenzoate, o-, m-, or p-methoxybenzoate, chlorobenzoate and naphthoate.

When the reaction of the invention is carried out in the presence of an organic carboxylic acid to be described hereinbelow or an aqueous solution thereof as the organic liquid medium described above, the aforementioned organic carboxylates of palladium can be formed in the reaction system of the present invention. Such organic carboxylates are utilized similarly as the catalyst for the reaction of the invention. The compounds which can form organic carboxylates of palladium in the reaction system of the invention may be any of those which can form salts by reaction with the aforementioned organic carboxylic acids. The preferred examples are inorganic compounds of palladium such as palladium oxides, hydroxides, nitrates or perchlorates, and suitable organic compounds of palladium.

In the present invention, β-diketo complexes of palladium can also be used as effective catalysts. The β-diketo complexes that can be used in the invention mean the palladium complexes having a keto and/or enol type β-diketo group as a ligand, the group being expressed by the following formula

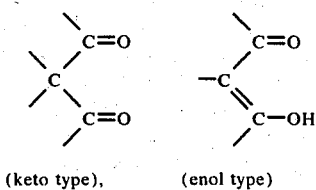

(keto type), (enol type)

Examples of β-diketo complexes of palladium include, for instance, β-diketone complexes of palladium, β-ketoester complexes of palladium, and β-keto acid complexes of palladium. The β-diketo complexes of palladium are prepared by reacting palladium compounds capable of forming β-diketo complexes, such as organic carboxylates of palladium described above or a nitrate, perchlorate, chloride, oxide, or hydroxide of palladium, with β-diketo group-containing compounds such as β-diketone, β-diketo ester, β-diketo acid or salts of these (the salts of an alkali metal such as sodium and potassium) which will be described hereinafter.

Examples of β-diketones include, for instance, acetylacetone, propionylactone, butylacetone, isobutyrylacetone, caproylacetone, C-methylacetylacetone, tetraacetylethane, benzoylacetone, dibenzoylmethane, trifluoroacetylacetone, hexafluoroacetylacetone, benzoyltrifluoroacetone, and β-naphthoyltrifluoroacetone. The β-keto esters include, for instance, acetoacetic acid ester, and trifluoroacetoacetic acid ester. As the β-keto acids, there can be named, for instance, acetoacetic acid, and trifluoroacetoacetic acid.

When the β-diketo complexes of palladium are used in the invention as catalysts, it is not absolutely necessary to add preformed β-diketo complexes of palladium, but the palladium compounds capable of forming the β-diketo complexes and the compounds containing a β-diketo grouping, such as β-diketones, β-keto esters or β-keto acids may be added to the reaction system of the present invention so as to form such β-diketo complexes of palladium in situ.

The aforementioned organic carboxylates of palladium and/or β-diketo complexes of palladium may be used singly or in combination of two or more as the catalyst for the reaction of the invention. It is possible to add suitable amounts of an organic carboxylate of palladium and a β-diketo group-containing compound to the reaction system of the invention, and in this way part of the organic carboxylate of palladium can be replaced by the β-diketo complex of palladium.

Research work has revealed that the β-diketo complex of palladium gives a higher yield of the biphenylpolycarboxylic acid ester as a final product per unit weight of palladium than the organic carboxylate of palladium. In the process of the present invention, the palladium catalyst having a high valency effective for the reaction is reduced by the oxidative coupling of the benzenecarboxylic acid esters to a lower valency state, but is immediately oxidized and regenerated by the molecular oxygen present in the reaction system, thereby maintaining necessary catalytic activity. Therefore, the palladium catalyst of the invention can be used even in very small amounts, and the amount of the catalyst used in the invention is not particularly restricted. In general, the amount of the catalyst is at least $1 \times 10^{-5}$ gram-atom, calculated as metallic palladium, for each gram-mol of the benzenecarboxylic acid ester, a particularly preferred range being 0.01-0.1 gram-atom. The upper limit of the amount of the palladium catalyst used in the invention is determined by economic and other factors, and not critical by itself.

The aforementioned organic carboxylates of palladium and/ or β-diketo complexes of palladium, when used conjointly with a zirconium compound, can give the intended biphenylpolycarboxylic acid esters in high yields with an increased catalytic activity. An especially outstanding rise in catalytic activity is observed when the zirconium compound is added to the organic carboxylate of palladium.

Such zirconium compound may be any of those which are partially soluble in the reaction system of the present invention, and suitable examples include, for instance, (a) organic carboxylates of zirconium, (b) oxycarboxylates of zirconium, (c) halogen compounds of zirconium, and (d) oxyhalogen compounds of zirconium. As the organic carboxylic acids which can provide carboxylic acid residues of the organic carboxylates of zirconium mentioned in (a) above, the same organic carboxylates as listed under paragraphs (i), (ii) and (iii) can be used. These organic carboxylates of zirconium are prepared by using the organic carboxylic acids and inorganic compounds capable of forming the salts of zirconium, such as the hydroxide, nitrate, perchlorate, and oxide of zirconium, and other suitable organic compounds of zirconium. Examples of the preferred organic carboxylates of zirconium include formate, acetate, propionate, n- or iso-butyrate, benzoate, and naphthenate.

The acids capable of providing the oxycarboxylic acid residues of the oxycarboxylates of zirconium may be any of the aforementioned organic carboxylic acids having an oxy group. Suitable examples of the oxycarboxylic acids include oxyformic acid, oxyacetic acid, oxypropionic acid, oxy n- or oxy iso-butyric acid. These oxycarboxylates of zirconium can be prepared by the same salt-forming reaction as used in the preparation of the organic carboxylates mentioned above.

As the halogen compounds of zirconium under (c) above, any of halides such as chloride, bromide, iodide, and fluoride of zirconium can be used, the chloride and bromide being preferred.

Examples of the oxyhalogen compounds of zirconium mentioned under (d) above include, for instance, oxychloride, oxybromide or oxyiodide of zirconium, and the oxychloride is preferred.

These zirconium compounds (a), (b), (c) and (d) may be formed in the reaction system of the present invention in the same way as in the case of the organic carboxylates and β-diketo complexes described above. These zirconium compounds can be present in the reaction system of the present invention either alone or in admixtures of two or more.

The amount of zirconium compound used in the process of the present invention is not particularly restricted. In general, the zirconium compound is used in an amount of preferably 0.01–100 gram-atoms, calculated as zirconium metal, per gram-atom of palladium of the palladium catalyst.

The catalyst comprising palladium and zirconium may further contain compounds of Pt, Rh, Ir, Au, or Ag, which are partially soluble in the reaction system of the present invention, especially organic acid salts of these compounds or the oxides or hydroxides of these compounds which can form organic acid salts in an organic carboxylic acid solvent.

According to the process of the invention, the conjoint use of the zirconium compound makes it possible to cause palladium to act catalytically, and to obtain the biphenylpolycarboxylic acid esters in high yields.

As previously stated, an inert organic liquid medium may be present in the reaction system of the present invention. The amount of such medium is usually not more than 100 times the weight of the benzenecarboxylic acid ester used as the starting material. A typical example of such inert organic liquid medium is an organic carboxylic acid. Examples of the preferred organic carboxylic acids are those which are liquid under the reaction conditions, preferably those which are liquid at room temperature, such as acetic acid, propionic acid, and n- or iso-butyric acid. Aromatic or alicyclic carboxylic acids such as benzoic acid or naphthenic acid may also be used. Aqueous solutions of these carboxylic acids containing not more than 15 % by weight of water can also be used as the reaction medium.

When the aforementioned β-diketo complex of palladium is used as the catalyst, an inert liquid compound which is liquid under the reaction conditions of the invention, preferably liquid at room temperature, such as aliphatic hydrocarbons, halogenated hydrocarbons, esters, ketones and ethers, can also be used as the reaction medium. Specific examples of such inert liquid compound are:

a. aliphatic hydrocarbons such as hexane, heptane and octane;
b. alicyclic hydrocarbons such as cyclopentane and cyclohexane;
c. chlorides and bromides of (a) or (b);
d. aliphatic ethers or alicyclic ethers such as methyl ether, ethyl ether, propyl ether, cyclopenty ether, and cyclohexyl ether;
e. esters of aliphatic carboxylic acids such as methyl acetate, ethyl propionate and cyclohexyl acetate; and
f. aliphatic ketones or alicyclic ketones such as acetone, di-t-butyl ketone and dicyclohexyl ketone.

In the present invention, the oxidative coupling of the benzenecarboxylic acid esters can be carried out catalytically by contacting the benzenecarboxylic acid esters with molecular oxygen in the liquid phase in the presence of the aforementioned palladium catalyst or in the presence of such palladium catalyst and the aforesaid zirconium compound, to thereby obtain biphenylpolycarboxylic acid esters. For ensuring the smooth process of the oxidative coupling reaction of the present invention, it is preferable to heat the reaction system of the present invention to a temperature of 90° to 300°C., especially 100° to 250°C. In general, the oxidative coupling reaction proceeds smoothyl under milder reaction conditions when the β-diketo complex of palladium is used as the catalyst than when the organic carboxylate of palladium is used. When the β-diketo complex of palladium is used as the catalyst, the reaction can proceed even at a temperature below 90°C. However, it is preferable to carry out the reaction at a temperature of at least 90°C., and good results are obtained within the temperature range of 100° to 160°C. When the catalyst is the organic carboxylate of palladium, it is advisable to carry our the reaction at a temperature in the range of 110° to 250°C., especially 120° to 250°C.

The molecular oxygen used in the practice of the present invention may be pure oxygen or a gas containing molecular oxygen which is diluted with an inert gas such as nitrogen, argon, helium or carbon dioxide, an example being air. It is preferred that such molecular oxygen or molecular oxygen-containing gas should be contacted with the benzenecarboxylic acid ester at a pressure of at least 0.2, preferably at least 1 atmosphere calculated as the partial pressure of oxygen. No specific upper limit is set on the partial pressure of oxygen in the molecular oxygen or molecular oxygen-containing gas. Too high a partial oxygen pressure, however, is commercially undesirable, and suitable pressures are generally below 300 atmospheres.

The process of the invention can be practised either by the batchwise, intermittent, continuous or circulating method. The wall of a reactor used in the invention may be of any materials which exhibit resistance to corrosion. If no solvent is used, the material may be iron. Generally, however, stainless steel is suitable, and examples of other materials that can be used include Hastelloy B, Hastelloy C, silver, nickel, titanium, titanium alloy, tantalum, glass lining and fluorine resin lining.

The biphenylpolycarboxylic acid esters obtained by the process of the invention are separated from the reaction mixture by such procedures as evaporation, distillation, filtration or centrifugation according to their physical characteristics, and can be purified by any means usually employed.

As previously described, benzenecarboxylic acid esters can be converted to the corresponding biphenylpolycarboxylic acid esters by a one-step catalytic reaction in accordance with the present invention, and a very small amount of the above described palladium catalyst or the palladium-zirconium catalyst exhibits an effective catalytic activity in the reaction, giving the biphenylpolycarboxylic acid esters in high yields and with high selectivities. The palladium or palladium-zirconium catalyst can be recovered, and recycled for further use.

The biphenylcarboxylic acid esters obtained by the process of the invention, either directly or after conversion to free carboxylic acids, can be used as the polybasic acid component of high molecular weight polyesters, polyamides or unsaturated polyesters.

The invention will further be described by the following Examples, which are intended to be illustrative rather than limitative. Unless otherwise specified, all parts in the examples are parts by weight.

EXAMPLE 1

An autoclave equipped with a stirrer was charged with 15 parts of methyl benzoate, 32 parts of acetic acid, and 0.42 parts of palladium acetate, and the reaction of the methyl benzoate was performed for 7 hours at 100°C. with the introduction of oxygen at a partial pressure of 60 Kg/cm$^2$G. Some 0.545 part of dimethyl diphenydicarboxylate, which corresponded to 108

EXAMPLE 2

An autoclave equipped with a stirrer was charged with 15 parts of methyl benzoate, 32 parts of acetic acid and 0.42 part of palladium acetate, and the reaction of the methyl benzoate was performed for 4 hours at 150°C. with the introduction of oxygen at a partial pressure of 100 Kg/cm$^2$G. As a result, 1.67 parts of dimethyl diphenyldicarboxylate, which corresponded to a yield of 83 mol% based on the methyl benzoate reacted, which in turn corresponded to 331 mol% of the palladium fed were obtained. This shows that the palladium salt acted catalytically.

EXAMPLE 3

The procedure of Example 2 was repeated except that the partial pressure of oxygen was 0.5 Kg/cm$^2$G and the reaction time was 10 hours. As a result 0.561 part of dimethyl diphenyldicarboxylate, which corresponded to 111 mol% of the palladium fed was obtained. This shows that the palladium salt acted catalytically.

COMPARATIVE EXAMPLE I

The procedure of Example 2 was repeated except that the partial pressure of oxygen was 0.1 atmosphere. As a result, 0.306 part of dimethyl diphenyldicarboxylate, which corresponded to 60.6 mol% of the palladium fed was obtained. This shows that the palladium salt did not act catalytically. This means that even if the reaction temperature is high, a low partial pressure of oxygen does not render the palladium salt catalytically active.

COMPARATIVE EXAMPLE 2

The procedure of Example 1 was repeated except that the reaction temperature was 80°C. As a result, 0.311 part of dimethyl diphenyldicarboxylate, which corresponded to 61.6 mol% of the palladium fed was obtained. This shows that even if the partial pressure of oxygen is high, a low reaction temperature does not render the palladium salt catalytically active.

EXAMPLE 4

An autoclave equipped with a stirrer was charged with 20 parts of methyl o-toluylate, 40 parts of acetic acid and 0.42 part of palladium acetate, and the reaction of the methyl o-toluylate was performed for 4 hours at 145°C. with the introducing of oxygen at a partial pressure of 80 Kg/cm$^2$G. As a result, 1.69 parts of dimethyl dimethyldiphenylcarboxylate, which corresponded to 303 mol% of the palladium salt fed were obtained.

EXAMPLE 5

The procedure of Example 4 was repeated except that methyl o-chlorobenzoate was used instead of the methyl o-toluylate and the reaction temperature was maintained at 150°C. As a result, 1.047 parts of dimethyl dichlorodiphenyldicarboxylate, which corresponded to 165.3 mol% of the palladium salt fed were obtained. This shows that the palladium salt acted catalytically.

EXAMPLE 6

A stainless steel autoclave equipped with a stirrer was charged with 15 parts of methyl benzoate, 32 parts of glacial acetic acid and 0.42 part of palladium stearate, and the reaction of the methyl benzoate was performed for 4 hours at 150°C. with the introduction of oxygen at a partial pressure of 100 Kg/cm$^2$G. Gaschromatographic analysis of the product indicated the formation of 1.24 parts of dimethyl diphenyldicarboxylate, which corresponded to a yield of 246 mol% based on the palladium stearate fed. This shows that the palladium salt acted catalytically.

EXAMPLE 7

The procedure of Example 6 was repeated except that 0.42 part of palladium benzoate was used as the palladium salt. As a result, 1.03 part of dimethyl diphenyldicarboxylate, which corresponded to a yield of 204 mol% based on the palladium benzoate fed. This shows that the palladium salt acted catalytically.

EXAMPLE 8

The procedure of Example 6 was repeated except that 0.42 part of palladium naphthenate was used as the palladium salt. As a result, 1.19 parts of dimethyl diphenyldicarboxylate, which corresponded to a yield of 236 mol% based on the palladium naphthenate fed was obtained. This shows that the palladium salt acted catalytically.

EXAMPLE 9

An autoclave equipped with a stirrer was charged with 15 parts of methyl benzoate, 32 parts of acetic acid and 0.42 part of palladium acetate, and the reaction of the methyl benzoate was performed for 10 hours at 90°C. with the introduction of oxygen at a partial pressure of 100 Kg/cm$^2$G. As a result, 0.538 part of dimethyl diphenyldicarboxylate, which corresponded to a yield of 107 mol% based on the palladium acetate fed was obtained. This shows that the palladium salt acted catalytically.

EXAMPLE 10

An autoclave equipped with a stirrer was charged with 15 parts of methyl benzoate, 32 parts of acetic acid and 0.42 part of palladium acetate, and the reaction of the methyl benzoate was performed for 30 minutes at 240°C. with the introduction of oxygen at a partial pressure of 60 Kg/cm$^2$G. As a result, 1.391 parts of dimethyl diphenyldicarboxylate, which corresponded to a yield of 276 mol% based on the palladium acetate fed were obtained. This shows that the palladium salt acted catalytically.

EXAMPLE 11

An autoclave equipped with a stirrer was charged with 15 parts of methyl benzoate and 0.287 part of acetylacetone palladium complex [Pd(AA)$_2$], and the reaction of the methyl benzoate was performed for 4 hours at a temperature of 130°C. with the introduction of oxygen at a partial pressure of 30 Kg/cm$^2$G. As a result, 4.573 parts of dimethyl diphenyldicarboxylate in a yield of 86 mol% based on the converted methyl benzoate were obtained.

The dimethyl diphenyldicarboxylate so produced corresponded to 1797 mol% based on the palladium salt fed, and this shows that the palladium salt acted catalytically.

EXAMPLE 12

The procedure of Example 11 was repeated except that the reaction temperature was 110°C. As a result, 1.340 parts of dimethyl diphenyldicarboxylate in a yield of 88 mol% based on the converted methyl benzoate were obtained. The dimethyl diphenyldicarboxylate so produced corresponded to 530 mol% based on the palladium salt fed, and this shown that the palladium salt acted catalytically.

EXAMPLE 13

An autoclave equipped with a stirrer was charged with 20 parts of methyl o-toluylate and 0.287 part of acetylacetone palladium complex [Pd(AA)$_2$], and the reaction of the methyl o-toluylate was performed for 4 hours at 130°C. with the introduction of oxygen at a partial pressure of 50 Kg/cm$^2$g. As a result, 3.925 parts of dimethyl dimethyldiphenyldicarboxylic acid, which corresponded to 1398 mol% based on the palladium salt fed were obtained.

EXAMPLE 14

An autoclave equipped with a stirrer was charged with 20 parts of methyl benzoate and 0.319 part of methyl acetoacetate-palladium complex, and the reaction of the methyl benzoate was performed for 4 hours at 120°C. with the introduction of oxygen at a partial pressure of 80 Kg/cm$^2$G. As a result 3.064 parts of dimethyl diphenyldicarboxylate, which corresponded to 1198 mol% based on the palladium salt fed were obtained.

EXAMPLE 15

An autoclave equipped with a stirrer was charged with 15 parts of methyl benzoate and 0.405 part of benzoyl acetone-palladium complex, and the reaction of the methyl benzoate was performed for 4 hours at 120°C. with the introduction of oxygen at a partial pressure of 60 Kg/cm$^2$G. As a result, 2.546 parts of dimethyl diphenyldicarboxylate, which corresponded to 998.3 mol% based on the palladium salt fed were obtained.

EXAMPLE 16

An autoclave equipped with a stirrer was charged with 15 parts of methyl benzoate, 32 parts of acetic acid, 0.42 part of palladium acetate [Pd(AcO)$_2$], and 2.105 parts of zirconyl acetate [ZrO(AcO)$_2$], and the reaction of the methyl benzoate was performed for 4 hours at 150°C. with the introduction of oxygen at a partial pressure of 60 Kg/cm$^2$G. As a result, 2.216 parts of dimethyl diphenyldicarboxylate, which corresponded to 83 mol% of the converted methyl benzoate, and 438.5 mol% based on the palladium salt fed were obtained. This shows that the palladium salt acted catalytically.

EXAMPLE 17

An autoclave equipped with a stirrer was charged with 15.0 parts of methyl benzoate, 0.42 part of palladium acetate, 2.105 parts of zirconyl acetate and 35 parts of acetic acid, and the reaction of methyl benzoate was performed for 4 hours at 115°C. with the introduction of oxygen at a pressure of 60 Kg/cm$^2$G. As a result, 0.692 part of dimethyl diphenyldicarboxylate, which corresponded to 136.9 mol% based on the palladium salt fed was obtained. This shows that the palladium salt acted catalytically.

EXAMPLE 18

The procedure of Example 16 was repeated except that the reaction temperature was maintained at 140°C. and the partial pressure of oxygen was 3 Kg/cm$^2$. As a result, 0.672 part of dimethyl diphenyldicarboxylate, which corresponded to 133 mol% of the palladium salt fed were obtained.

EXAMPLE 19

An autoclave equipped with a stirrer was charged with 15 parts of methyl o-toluylate, 32 parts of acetic acid, 0.21 part of palladium acetate and 1.053 parts of zirconyl acetate, and the reaction of the methyl o-toluylate was performed for 4 hours at 150°C. with the introduction of oxygen at a partial pressure of 100 Kg/cm$^2$G. As a result, 0.980 part of dimethyl dimethyl-diphenyldicarboxylate, which corresponded to 77 mol% of the converted methyl o-toluylate, and 352 mol% of the palladium salt fed was obtained.

EXAMPLE 20

An autocalve equipped with a stirrer was charged with 20 parts of methyl o-chlorobenzoate, 32 parts of acetic acid, 0.42 part of palladium acetate and 2.105 parts of zirconyl acetate, and the reaction of the methyl o-chlorobenzoate was performed for 4 hours at 150°C. with the introduction of oxygen at a partial pressure of 40 Kg/cm$^2$G. As a result, 1.413 parts of dimethyl dichlorodiphenyldicarboxylate, which corresponded to 223 mol% of the palladium salt fed were obtained. This shows that the palladium salt acted catalytically.

EXAMPLE 21

An autoclave equipped wih a stirrer was charged with 15 parts of dimethyl phthalate, 32 parts of glacial acetic acid, 2.105 parts of zirconium oxyacetate and 0.42 part of palladium acetate, and the reaction of the dimethyl phthalate was performed for 4 hours at 150°C. with the introduction of oxygen at a partial pressure of 100 Kg/cm$^2$G. A dimerized product of an amount corresponding to 130 mol% of the palladium acetate fed was obtained. This shows that the palladium salt acted catalytically.

EXAMPLE 22

The procedure of Example 21 was repeated except that 15 parts of ethyl benzoate was used instead of the dimethyl phthalate. A dimerized product of an amount corresponding to 420 mol% of the palladium acetate fed was obtained. This shows that the palladium salt acted catalytically.

EXAMPLE 23

The procedure of Example 21 was repeated except that 15 parts of propyl benzoate was used instead of the dimethyl phthalate. A dimerized product of an amount corresponding to 430 mol% of the palladium acetate fed was obtained. This shows that the palladium salt acted catalytically.

EXAMPLE 24

A stainless steel autoclave equipped with a stirrer was charged with 15 parts of methyl benzoate, 32 parts of glacial acetic acid, 0.42 part of palladium acetate and 2.105 parts of zirconium oxystearate, and the reaction of the methyl benzoate was performed for 4 hours at 150°C. with the introduction of oxygen at a partial pressure of 100 Kg/cm²G. As a result, 1.745 parts of dimethyl diphenyldicarboxylate, which corresponded to a yield of 346 mol% based on the palladium acetate fed. This shows that the palladium salt acted catalytically.

EXAMPLE 25

The procedure of Example 24 was repeated except that 2.105 parts of zirconium oxybenzoate was used instead of the zirconium oxystearate. As a result, 1.546 parts of dimethyl diphenyldicarboxylate, which corresponded to 307 mol% based on the palladium acetate fed were obtained. This shows that the palladium salt acted catalytically.

EXAMPLE 26

The procedure of Example 24 was repeated except that 2.105 parts of zirconium oxynaphthenate was used instead of the zirconium oxystearate. As a result, 1.813 parts of dimethyl diphenyldicarboxylate, which corresponded to a yield of 360 mol% based on the palladium acetate fed were obtained. This shows that the palladium salt acted catalytically.

EXAMPLE 27

An autoclave equipped with a stirrer was charged with 20 parts of methyl benzoate and 0.319 part of palladium acetate, and the reaction of the methyl benzoate was performed for 4 hours at 120°C. with the introduction of oxygen at a partial pressure of 80 Kg/cm²G. As a result, 2.538 parts of dimethyl diphenyldicarboxylate, which corresponded to a yield of 504 mol% based on the palladium acetate fed were obtained. This shown that the palladium salt acted catalytically.

EXAMPLE 28

An autoclave equipped with a stirrer was charged with 15 parts of methyl benzoate, 0.287 part of acetylacetone-palladium complex and 0.21 part of palladium acetate, and the reaction of the methyl benzoate was performed for 4 hours at 130°C. with the introduction of oxygen at a partial pressure of 30 Kg/cm²G. As a result, 6.192 parts of dimethyl diphenyldicarboxylate, which corresponded to a yield of 614 mol% based on the palladium salt fed were obtained. This shows that the palladium salt acted catalytically.

EXAMPLE 29

An autoclave equipped with a stirrer was charged with 15 parts of methyl benzoate, 0.287 parts of acetylacetone-palladium complex, 0.21 part of palladium acetate and 1.052 part of zirconium oxyactate, and the reaction of the methyl benzoate was performed for 4 hours at 130°C. with the introduction of oxygen at a partial pressure of 30 Kg/cm²G. As a result, 6.341 parts of dimethyl diphenyldicarboxylate, which corresponded to a yield of 629 mol% based on the palladium salt fed were obtained. This shows that the palladium salt acted catalytically.

EXAMPLE 30

An autoclave equipped with a stirrer was charged with 15 parts of methyl o-chlorobenzoate and 0.287 part of acetylacetone-palladium complex, and the reaction of the methyl o-chlorobenzoate was performed for 4 hours at 130°C. with the introduction of oxygen at a partial pressure of 30 Kg/cm²G. As a result, 3.712 parts of dimethyl dichlorodiphenyldicarboxylate, which corresponded to a yield of 586 mol% based on the palladium complex fed were obtained. This shows that the palladium complex acted catalytically.

EXAMPLE 31

An autoclave equipped with a stirrer was charged with 15 parts of methyl o-methoxybenzoate and 0.287 part of acetylacetone-palladium complex, and the reaction of the methyl o-methoxybenzoate was performed for 4 hours at 170°C. with the introduction of oxygen at a partial pressure of 30 Kg/cm²G. As a result, 5.198 parts of dimethyl dimethoxydiphenyldicarboxylate, which corresponded to a yield of 840 mol% based on the palladium complex fed were obtained. This shows that the palladium complex acted catalytically.

What we claim is:

1. A process for producing biphenylpolycarboxylic acid esters which comprises contacting a benzenecarboxylic acid ester having 1 or 2 carboxylic acid ester groups having at least one hydrogen atom bonded to the nuclear carbon atom with molecular oxygen or a molecular oxygen-containing gas in liquid phase at a temperature of 110°– 250°C., under a partial pressure of molecular oxygen of 0.2 – 300 atmospheres and in the presence of a catalyst consisting essentially of at least one compound selected from at least one of the group consisting of salts of palladium which are aliphatic mono-carboxylates having 1 to 20 carbon atoms, alicyclic carboxylates, benzenecarboxylates, or naphthalenecarboxylates, and said catalyst being at least partially soluble in the reaction system.

2. The process of claim 1 wherein said benzenecarboxylic acid ester is a compound expressed by the following formula

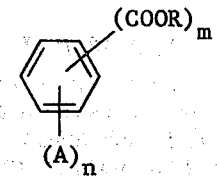

wherein R represents an alkyl group having 1–4 carbon atoms; $m$ is an integer of 1 or 2; A represents an alkyl group having 1–4 carbon atoms, an alkoxy group group having 1–4 carbon atoms, or a halogen atom; $n$ is a positive integer of 0 to 3; the sum of $m$ and $n$ does not exceed 4; and when $n$ is 0, $-(A)_n$ represents a hydrogen atom.

3. The process of claim 1 wherein said oxidative dimerization is carried out in the presence of an inert organic liquid medium of an amount not in excess of 100 times the weight of said benzenecarboxylic acid ester.

4. The process of claim 3 wherein said organic liquid medium is an organic carboxylic acid or its aqueous solution having not more than 15% by weight of water.

5. The process of claim 1 wherein the catalyst is present in an amount of at least $1 \times 10^{-5}$ gram-atom, calculated as metallic palladium, for each gram-mol of the benzenecarboxylic acid ester.

6. The process of claim 5 wherein the catalyst is present in an amount of from 0.01 to 0.1 gram-atom, calculated as metallic palladium, for each gram-mol of the benzenecarboxylic acid ester.

7. The process of claim 1 in which the minimum temperature is 120°C.

8. The process of claim 1 in which the minimum pressure is 1.0 atmosphere.

* * * * *

UNITED STATES PATENT AND TRADEMARK OFFICE
CERTIFICATE OF CORRECTION

PATENT NO. : 3,983,159
DATED : September 28, 1976
INVENTOR(S) : Yataro Ichikawa et al.

It is certified that error appears in the above-identified patent and that said Letters Patent are hereby corrected as shown below:

Insert the following Foreign Application Priority Data:

-- July 24, 1969 JAPAN ......................44-58811
   July 25, 1969 JAPAN ......................44-58844
   July 25, 1969 JAPAN ......................44-58847 --

Claim 2, column 12, line 45, delete "group" in the third instance.

Signed and Sealed this

Twenty-first Day of December 1976

[SEAL]

Attest:

RUTH C. MASON
Attesting Officer

C. MARSHALL DANN
Commissioner of Patents and Trademarks